(12) United States Patent
Chen et al.

(10) Patent No.: US 7,501,428 B2
(45) Date of Patent: Mar. 10, 2009

(54) QUINAZOLINE THIAZOLINONES

(75) Inventors: Li Chen, Shanghai (CN); Shaoqing Chen, Bridgewater, NJ (US); Jin-Jun Liu, Warren Township, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 511 days.

(21) Appl. No.: 11/244,028

(22) Filed: Oct. 5, 2005

(65) Prior Publication Data

US 2006/0084804 A1    Apr. 20, 2006

Related U.S. Application Data

(60) Provisional application No. 60/681,079, filed on May 13, 2005, provisional application No. 60/618,612, filed on Oct. 14, 2004.

(51) Int. Cl.
*A61K 31/517* (2006.01)
*C07D 239/95* (2006.01)

(52) U.S. Cl. .................................. 514/266.2; 544/284
(58) Field of Classification Search ............. 514/266.2; 544/284

See application file for complete search history.

(56) References Cited

U.S. PATENT DOCUMENTS

2002/0165259 A1    11/2002    Rawlins et al.

FOREIGN PATENT DOCUMENTS

| WO | WO 2004/006916 | 1/2004 |
| WO | WO 2004/007491 | 1/2004 |
| WO | WO 2004/047760 A2 | 6/2004 |
| WO | WO 2005/011686 | 2/2005 |

*Primary Examiner*—James O Wilson
*Assistant Examiner*—Tamthom N Truong
(74) *Attorney, Agent, or Firm*—George W. Johnston; Patricia S. Rocha-Tramaloni; David E. Wildman

(57) ABSTRACT

Quinazoline thiazolinone derivatives which demonstrate CDK1 antiproliferative activity and are useful as anti-cancer agents.

22 Claims, No Drawings

QUINAZOLINE THIAZOLINONES

PRIORITY TO RELATED APPLICATIONS

This application claims the benefit of U.S. Provisional Application No. 60/618,610, filed Oct. 14, 2004, and U.S. Provisional Application No. 60/681,079, filed May 13, 2005. The entire contents of the above-identified applications are hereby incorporated by reference.

FIELD OF THE INVENTION

The field of this invention relates to quinazoline thiazolinone derivatives which demonstrate CDK1 antiproliferative activity and are useful as anti-cancer agents.

BACKGROUND OF THE INVENTION

Cyclin-dependent kinases (CDKs) are serine-threonine protein kinases that play critical roles in regulating the transitions between different phases of the cell-cycle, such as the progression from a quiescent stage in $G_1$ (the gap between mitosis and the onset of DNA replication for a new round of cell division) to S (the period of active DNA synthesis), or the progression from $G_2$ to M phase, in which active mitosis and cell-division occurs. (See, e.g., the articles compiled in *Science*, 274:1643-1677 (1996); and *Ann. Rev. Cell Dev. Biol.*, 13:261-291 (1997)). CDK complexes are formed through association of a regulatory cyclin subunit (e.g., cyclin A, B1, B2, D1, D2, D3 and E) and a catalytic kinase subunit (e.g., CDK1, CDK2, CDK4, CDK5 and CDK6). As the name implies, the CDKs display an absolute dependence on the cyclin subunit in order to phosphorylate their target substrates, and different kinase/cyclin pairs function to regulate progression through specific phases of the cell-cycle.

As seen above, these protein kinases are a class of proteins (enzymes) that regulate a variety of cellular functions. This is accomplished by the phosphorylation of specific amino acids on protein substrates resulting in conformational alteration of the substrate protein. The conformational change modulates the activity of the substrate or its ability to interact with other binding partners. The enzyme activity of the protein kinase refers to the rate at which the kinase adds phosphate groups to a substrate. It can be measured, for example, by determining the amount of a substrate that is converted to a product as a function of time. Phosphorylation of a substrate occurs at the active-site of a protein kinase.

In view of the above properties, these kinases play an important part in the propagation of growth factor signal transduction that leads to cellular proliferation, differentiation and migration. Fibroblast growth factor (FGF) and vascular endothelial growth factor (VEGF) have been recognized as important mediators of tumor promoted angiogenesis. VEGF activates endothelial cells by signaling through two high affinity receptors, one of which is the kinase insert domain-containing receptor (KDR). (See, Hennequin L. F. et. al., *J. Med. Chem.* 45(6):1300 (2002)). FGF activates endothelial cells by signaling through the FGF receptor (FGFR). Solid tumors depend upon the formation of new blood vessels (angiogenesis) to grow. Accordingly, inhibitors of the receptors FGFR and KDR that interfere with the growth signal transduction, and thus slow down or prevent angiogenesis, are useful agents in the prevention and treatment of solid tumors. (See, Klohs W. E. et. al., *Current Opinion in Biotechnology*, 10:544 (1999).

Because CDKs, such as CDK1, serve as general activators of cell division, inhibitors of CDK1 can be used as antiproliferative agents. These inhibitors can be used for developing therapeutic intervention in suppressing deregulated cell cycle progression.

SUMMARY OF THE INVENTION

The present invention provides compounds of the formula:

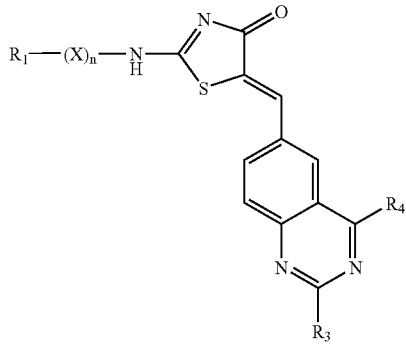

wherein $R_1$ is hydrogen, lower alkyl or

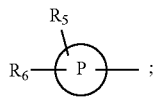

X is selected from lower alkylene, cyclolower alkylene containing from 3 to 6 carbon atoms and hydroxy lower alkylene;

is selected from an aryl ring, cyclolower alkyl ring containing from 3 to 6 carbon atoms, a 4 to 6 membered heterocycloalkyl ring containing from 3 to 5 carbon atoms and from 1 to 2 hetero atoms selected from the group consisting of oxygen, nitrogen and sulfur, and a 5 or 6 membered heteroaromatic ring containing from 1 to 2 hetero atoms selected from the group consisting of oxygen, sulfur and nitrogen;

$R_5$ and $R_6$ are independently selected from the group consisting of hydrogen, hydroxy, hydroxy-lower alkyl, lower alkyl, halogen, perfluro-lower alkyl and lower alkoxy;

$R_3$ is selected from hydrogen, —$NHR_7$, and

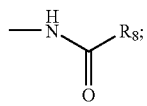

$R_4$ is selected from hydrogen, lower alkyl, and —$O(CH_2CH_2O)_y$—$R_{10}$;

$R_7$ is hydrogen or lower alkyl;

$R_8$ and $R_{10}$ are lower alkyl;

n is an integer from 0 to 1; and y is an integer of from 0 to 3;

with the proviso that when n is 0 and $R_1$ is hydrogen or lower alkyl then $R_3/R_4$ cannot both be hydrogen; and N-oxides of compounds where $R_1$ contains a nitrogen in the heteroaromatic ring, sulfones where $R_1$ contains a sulfur in the heterocycloalkyl ring or heteroaromatic ring, and pharmaceutically acceptable salts thereof.

The compounds of formula I inhibit the activity of CDKs, particularly, CDK1. These inventive agents and pharmaceutical compositions containing such agents are useful in treating various diseases or disorder states associated with uncontrolled or unwanted cellular proliferation, such as cancer, autoimmune diseases, viral diseases, fungal diseases, neurodegenerative disorders and cardiovascular diseases.

Inhibiting and/or modulating the activity of CDKs, particularly CDK1, makes these compounds of formula I and compositions containing these compounds useful in treating diseases medicated by kinase activity, particularly as anti-tumor agents in treating cancers.

DETAILED DESCRIPTION OF THE INVENTION

As pointed out herein, the compounds of formula I are potential anti-proliferation agents and are useful for mediating and/or inhibiting the activity of CDKs, particularly CDK1, thus providing anti-tumor agents for treatment of cancer or other diseases associated with uncontrolled or abnormal cell proliferation.

Among the preferred compounds of formula I are compounds where n is 0. These compounds include the compounds of the formula:

I-A wherein $R_1'$ is hydrogen or a lower alkyl;
$R_4'$ is lower alkyl or —O(CH$_2$CH$_2$O)$_y$—R$_{10}$; and
$R_3$, $R_{10}$ and y are as above; and pharmaceutically acceptable salts thereof.

The compounds of formula I where n is 0 also includes the compounds of the formula:

I-B wherein
$R_1''$ is $R_3$, $R_4$, $R_5$, $R_6$ and are as above; and
N-oxides of compounds where $R_1''$ contains a nitrogen in the heteroaromatic ring, sulfones where $R_1''$ contains a sulfur in the hetero ring or heteroaromatic ring; and pharmaceutically acceptable salts thereof.

When n in the compound of formula I is 1, this compound has the formula:

I-C wherein
$R_1''$, X, $R_3$, $R_4$ and are as above; or
N-oxides of compounds where $R_1''$ contains a nitrogen in the heteroaromatic ring, sulfones where $R_1''$ contains a sulfur in the hetero ring or heteroaromatic ring; or pharmaceutically acceptable salts thereof.

In compounds I, I-B and I-C, where $R_1$ and $R_1''$ are substituents containing an aryl moiety, the preferred aryl moiety is phenyl. As used herein the halogen includes all four halogens such as chlorine, fluorine, bromine and iodine.

As used in the specification, the term "lower alkyl", alone or in combination, means a monovalent straight or branched-chain saturated hydrocarbon alkyl group containing from one to six carbon atoms, such as methyl, ethyl, n-propyl, isopropyl, n-butyl, sec-butyl, isobutyl, tert-butyl, n-pentyl, n-hexyl and the like.

The term "cycloalkyl" means a cyclolower alkyl substituent which designates a monovalent unsubstituted 3- to 6-membered saturated carbocyclic hydrocarbon ring. Among the preferred cycloalkyl substituents are cyclopropyl, cyclobutyl, cyclohexyl, etc.

The term "lower alkoxy" means a straight-chain or branched-chain alkoxy group formed from lower alkyl containing form one to six carbon atoms, such as methoxy, ethoxy, n-propoxy, isopropoxy, n-butoxy, tert-butoxy and the like.

The term "aryl" means a monovalent mono- or bicyclic unsubstituted aromatic hydrocarbon ring, such as phenyl or naphthyl, with phenyl being preferred.

The term "heterocycloalkyl" refers to a 4 to 6 membered monocyclic saturated ring containing 3 to 4 carbon atoms and one or two hetero atoms selected from the group consisting of oxygen, nitrogen and sulfur. Among the preferred heterocyclic alkyl groups are included mopholinyl, tetrahydro, thiopyranyl or tetrahydro pyranyl.

The term "heteroaromatic ring" refers to a monovalent 5 or 6 membered monocyclic heteroaromatic ring containing from 4 to 5 carbon atoms and from 1 to 2 hetero atoms selected from the group consisting of oxygen, nitrogen and sulfur. Among the preferred heteroaromatic groups are included thiopenyl, thioazole, pyridinyl, furanyl, etc.

The term "lower alkylene" designates a divalent saturated straight or branch chain hydrocarbon substituent containing from one to six carbon atoms.

The term "hydroxy lower alkylene" designates a lower alkylene substituent substituted, preferably monosubstituted, with a hydroxy group where an amido lower alkylene is used, this designates a lower alkylene substituent as set forth hereinbefore substituted with an amido substituent.

The term "cyclo lower alkylene" designates a cyclo lower alkenyl substituent which is a divalent unsubstituted 3 to 6 membered saturated carbocyclic hydrocarbon ring. Among the preferred cycloalkylene substituents are cyclopropenyl and cyclobutenyl.

The term "perfluoro-lower alkyl" means any lower alkyl group wherein all the hydrogens of the lower alkyl group are substituted or replaced by fluorine. Among the preferred perfluoro-lower alkyl groups are trifluoromethyl, pentafluoroethyl, heptafluoropropyl, etc with trifluoromethyl being especially preferred.

The term "pharmaceutically acceptable salts" refers to conventional acid-addition salts or base-addition salts that retain the biological effectiveness and properties of the compounds of formulas I, I-A, I-B and I-C are formed from suitable non-toxic organic or inorganic acids, or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, maleic acid, lactic acid, fumaric acid, and the like. Sample base-addition salts include those derived from ammonium, potassium, sodium and, quaternary ammonium hydroxides, such as for example, tetramethylammonium hydroxide. The chemical modification of a pharmaceutical compound (i.e., drug) into a salt is a technique well known to pharmaceutical chemists to obtain improved physical and chemical stability, hygroscopicity, flowability and solubility of compounds. See, e.g., H. Ansel et al., *Pharmaceutical Dosage Forms and Drug Delivery Systems* (6th Ed. 1995) at pp. 196 and 1456-1457.

In accordance with this invention, the compounds of formula I can be prepared from a compound of the formula:

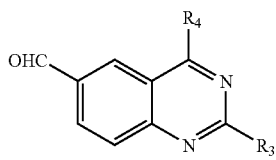

wherein $R_3$ and $R_4$ are as above.

The compound of formula II is converted to the compound of formula I via the following reaction scheme.

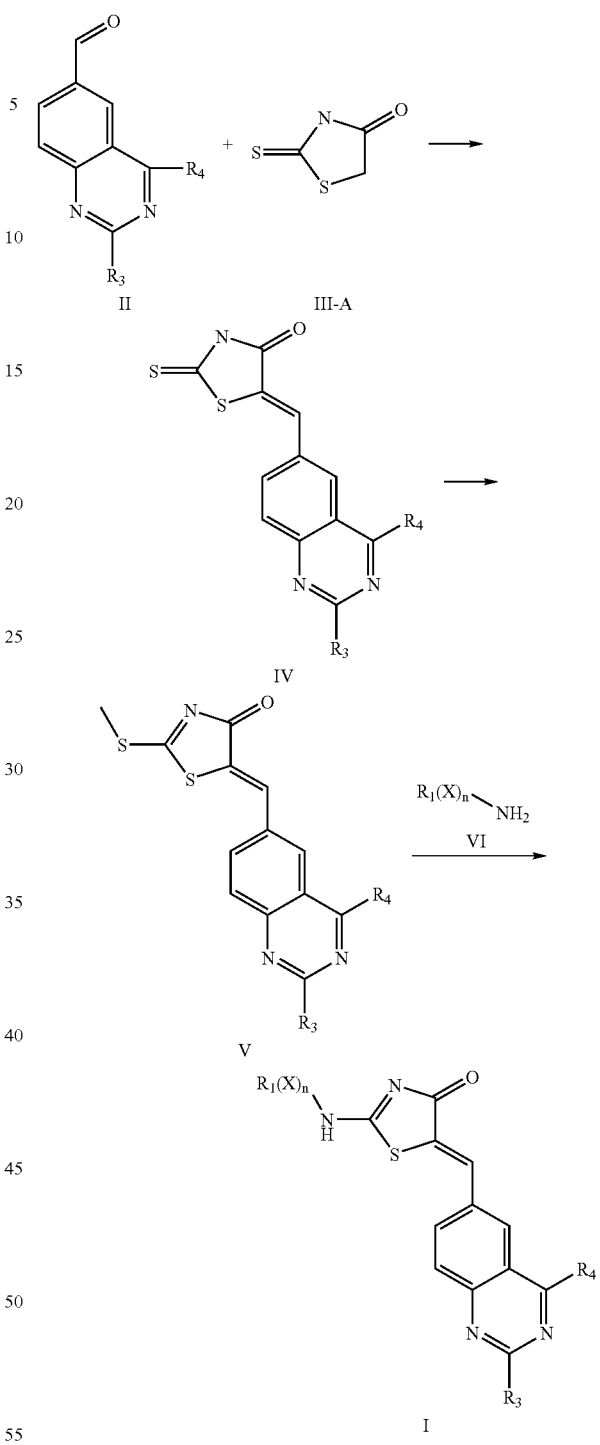

wherein
X, $R_1$, $R_3$, $R_4$ and n are as above.

In accordance with this invention, the compound of formula II is reacted with the compound of formula III-A [rhodanine (2-thio-4-thiazolin-4-one)] via a Knoevenegel reaction to produce the compound of formula IV. Any of the conditions conventional in carrying out Knoevenegel reaction can be utilized in carrying out this condensation. Generally this reaction is carried out at reflux temperature in the presence of alkali metal acetate and acetic acid. In the next step of this synthesis, the resulting substituted thiazolidine of formula IV is treated with a methylating agent to methylate the thio group on the compound of formula IV to produce the compound of formula V. The preferred methylating agent is iodomethane. This reaction is carried out in an organic amine base such as diisopropylethylamine (DIEA). In carrying out this reaction temperature and pressure are not critical and this reaction can be carried out at room temperature and atmospheric pressure. In fact in carrying out this reaction, any of the conditions conventional in methylating a thio group can be used.

In the next step of this synthesis, the compound of formula V is reacted with the compound of formula VI to produce the compound of formula I. The compound of formula VI is an amine and any means conventionally used in amine substitution of the methylthio group can be used in carrying out this reaction. In accordance with one embodiment this substitution is carried out by reacting the compound of formula VI with the compound of formula V in the presence of a conventional solvent such as acetonitrile. Generally this reaction is carried out in the presence of an amine base such as diisopropylethylamine.

On the other hand, the compound of formula I can be prepared by reacting the compound of formula II with a compound of the formula:

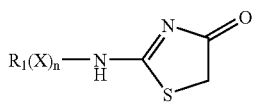  VII wherein $R_1$ is as above.

The reaction of the compound of formula VII with the compound of formula II to produce the compound of formula I, is carried out in an organic solvent such as benzene or toluene at high temperature of from 100° C. to 200° C. in a closed system. In this manner, this reaction is carried out under high temperatures and pressure. The compound of formula VII can be directly formed by direct replacement thorough reacting the compound of the formula

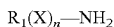  VI wherein $R_1$, X and n are as above, with a compound of the formula III-A. The replacement reaction is generally carried out in the presence of an activator and an amine base. Among the preferred activators is mercuric chloride. This reaction is carried out in an inert organic solvent. Any conventional inert organic solvent such as acetonitrile, methylene chloride, etc. can be utilized. In carrying out this reaction, an amine base, such as diisoproprylethylamine, is used. In carrying out this reaction, temperature and pressure are not critical and this reaction can be carried out at room temperature and atmospheric pressure. In carrying out this reaction, any conventional method of replacing a mercapto group with an amine can be utilized.

In accordance with an embodiment of this in the compound of formula II, when $R_4$ is $-O(CH_2CH_2O)_y-R_{10}$, and $R_{10}$ and y are as above has the formula:

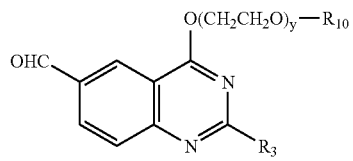  II-A where y, $R_3$ and $R_{10}$ are as above.

The compound of formula II-A can be prepared from a compound of the formula

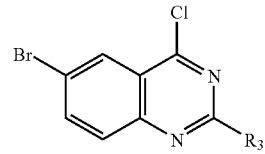  X by reacting with a compound of the formula, $NaO(CH_2CH_2O)_y-R_{10}$  XI where y and $R_{10}$ are as above, to produce

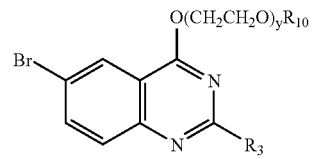  XII where $R_{10}$, $R_3$ and y are as above

The reaction of the compound of formula X with the compound of formula XI to produce a compound XII is carried out by conventional mean of reacting a chloride with an alkali metal alkoxide to produce an ether. Any conventional mean of reacting a chloride with an alkali metal alkoxide can be used to form the compound of formula XII. In the next step of this reaction to produce the compound of formula II-A using formylation reaction to convert the bromo group to the CHO substituent on the phenyl ring. This reaction is carried out by reacting the compound of formula XI with carbon monoxide under pressure in the presence of diphenyl propyl phosphine (dpp) and a base utilizing palladium acetate as catalyst at temperature of from 60 to 100° C. Pressures generally from 70 to 80 psi are utilized in carrying out this reaction. Any conventional method of formylation reaction to convert a halide group on a phenyl ring by means of reaction with carbon monoxide can be utilized to carry out this conversion.

Where $R_3$ is the compound of formula X is $-NHR_7$, this compound has the formula:

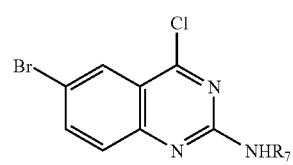  X-A where $R_7$ is as above.

The compound of formula X-A can be prepared from a compound of the formula:

XV

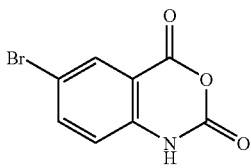

by reacting the compound of formula XV (the synthesis of the compound of formula is described in example 12b) with a compound of formula:

XVI

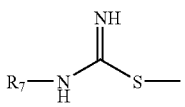

where $R_7$ is as above, to produce the compound of formula:

XVII

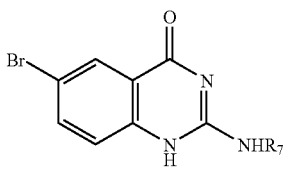

where $R_7$ is as above which can be converted to the compound of formula X-A.

The compound of formula XV converted to the compound of formula XVII by reacting the compound of formula XV with the compound of formula XVI. This reaction is carried out by adding the compound of formula XVI to the compound of formula XV in the presence of an inert solvent. Any conventional inert solvent such as acetonitrile and water can be utilized as the reaction medium. The reaction can be carried out by heating the resulting mixture to reflux. The compound of formula XVII can be converted to the compound of formula X-A by treating with a conventional chlorinating agent such as phosphorous oxychloride. This reaction is carried out by heating to reflux generally under a nitrogen atmosphere.

The compound of formula XVI is either commercially available or can be prepared from their corresponding thiourea, $R_7$—NH—C(=S)—$NH_2$, with alkylating reagent, such as iodomethane.

In the compounds of formula I, I-B and I-C, preferred are those class of compounds where $R_3$ and $R_4$ are both hydrogen and those class of compounds where $R_3$ is —$NHR_7$ and $R_4$ is hydrogen or —$O(CH_2CH_2O)_y$—$R_{10}$.

In compound I and I-B where n is 1 the substituents for $R_1$ and $R_1'$ are aryl rings the preferred ring is a phenyl which can be unsubstituted or substituted with this substituents defined as $R_5$ and $R_6$.

One embodiment of the compound of formula I-A are those compounds where $R_1'$ is hydrogen. Among these class of compounds are those compounds where $R_4'$ is —$O(CH_2CH_2O)_y$—$R_{10}$.

Another embodiment of this invention are the compounds of formula I-B where n is 0 and

is phenyl or a heteroaromatic ring containing from 1 to 2 heteroatoms. The preferred heteroaromatic rings are those rings containing two hetero atoms one being nitrogen and the other being sulfur, and thiazole being most preferred. Another preferred heteroaromatic ring is that having one hetero atom, preferably sulfur, with thiophene being especially preferred.

In accordance with another embodiment of the compound of formula I-B where n is 1 are those compounds where X is a lower alkylene substituent. This embodiment includes a class of compounds where $R_1$ contains a phenyl ring which can be phenyl or substituted phenyl. Another class of compounds are those compounds where n is 1 are those compounds where X is a lower alkylene substituent and $R_1'$ is a heteroaromatic ring. The preferred heteroaromatic rings are those which contain two hetero atoms, one being nitrogen and the other being sulfur, and thiazole being most preferred. Another preferred heteroaromatic ring are those containing one heteroatom, preferably sulfur, with thiophene being especially preferred. In this preferred class of compounds $R_4$ is preferably —$O(CH_2CH_2O)_y$—$R_{10}$.

Another embodiment of the compound of formula I-B where n is 1 are those compounds where X is a hydroxy-lower alkylene substituent. In this class of compounds is included those compounds where $R_1$ is a heteroaromatic ring. The preferred heteroaromatic rings are those which contain two hetero atoms one being nitrogen and the other being sulfur, with thiazole being most preferred. Another preferred heteroaromatic ring is that having one heteroatom, preferably sulfur, with thiophene being especially preferred. In this preferred class of compounds, $R_4$ is preferably —$O(CH_2CH_2O)_y$—$R_{10}$. Another preferred class of compounds where n is 1 and X' is a hydroxy-lower alkylene substituent are those compounds where $R_1$ is a phenyl ring which can be phenyl or substituted phenyl. In this preferred class of compounds, $R_4$ is preferably —$O(CH_2CH_2O)_y$—$R_{10}$.

Pharmaceutical compositions according to the invention may, alternatively or in addition to a compound of Formula I, comprise as an active ingredient pharmaceutically acceptable prodrugs, pharmaceutically active metabolites, and pharmaceutically acceptable salts of such compounds and metabolites. Such compounds, prodrugs, multimers, salts, and metabolites are sometimes referred to herein collectively as "active agents" or "agents."

In the case of agents that are solids, it is understood by those skilled in the art that the inventive compounds and salts may exist in different crystal or polymorphic forms, all of which are intended to be within the scope of the present invention and specified formulas.

Therapeutically effective amounts of the active agents of the invention may be used to treat diseases mediated by modulation or regulation of the protein kinases CDK1. An "effective amount" is intended to mean that amount of an agent that significantly inhibits proliferation and/or prevents de-differentiation of a eukaryotic cell, e.g., a mammalian, insect, plant or fungal cell, and is effective for the indicated utility, e.g., specific therapeutic treatment.

The amount of a given agent that will correspond to such an amount will vary depending upon factors such as the particular compound, disease condition and its severity, the identity (e.g., weight) of the subject or host in need of treatment, but can nevertheless be routinely determined in a manner known in the art according to the particular circumstances surrounding the case, including, e.g., the specific agent being administered, the route of administration, the condition being treated, and the subject or host being treated. "Treating" is intended to mean at least the mitigation of a disease condition in a subject such as mammal (e.g., human), that is affected, at least in part, by the activity of CDK1 protein kinase includes: preventing the disease condition from occurring in a mammal, particularly when the mammal is found to be predisposed to having the disease condition but has not yet been diagnosed as having it; modulating and/or inhibiting the disease condition; and/or alleviating the disease condition.

The present invention is further directed to methods of modulating or inhibiting protein kinase CDK1 activity, for example in mammalian tissue, by administering the inventive agent. The activity of agents as anti-proliferatives is easily measured by known methods, for example by using whole cell cultures in an MTT assay. The activity of the inventive agents as modulators of CDK1 protein kinase activity may be measured by any of the methods available to those skilled in the art, including in vivo and/or in vitro assays. Examples of suitable assays for activity measurements include those described in International Publication No. WO 99/21845; Parast et al., Biochemistry, 37, 16788-16801 (1998); Connell-Crowley and Harpes, Cell Cycle: Materials and Methods, (Michele Pagano, ed. Springer, Berlin, Germany)(1995); International Publication No. WO 97/34876; and International Publication No. WO 96/14843. These properties may be assessed, for example, by using one or more of the biological testing procedures set out in the examples below.

The active agents of the invention may be formulated into pharmaceutical compositions as described below. Pharmaceutical compositions of this invention comprise an effective modulating, regulating, or inhibiting amount of a compound of Formula I and an inert, pharmaceutically acceptable carrier or diluent. In one embodiment of the pharmaceutical compositions, efficacious levels of the inventive agents are provided so as to provide therapeutic benefits involving anti-proliferative ability. By "efficacious levels" is meant levels in which proliferation is inhibited, or controlled. These compositions are prepared in unit-dosage form appropriate for the mode of administration, e.g., parenteral or oral administration.

An inventive agent can be administered in conventional dosage form prepared by combining a therapeutically effective amount of an agent (e.g., a compound of Formula I) as an active ingredient with appropriate pharmaceutical carriers or diluents according to conventional procedures. These procedures may involve mixing, granulating and compressing or dissolving the ingredients as appropriate to the desired preparation.

The pharmaceutical carrier employed may be either a solid or liquid. Exemplary of solid carriers are lactose, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time-delay or time-release material known in the art, such as glyceryl monostearate or glyceryl distearate alone or with a wax, ethylcellulose, hydroxypropylmethylcellulose, methyl methacrylate and the like.

A variety of pharmaceutical forms can be employed. Thus, if a solid carrier is used, the preparation can be tableted, placed in a hard gelatin capsule in powder or pellet form or in the form of a troche or lozenge. The amount of solid carrier may vary. If a liquid carrier is used, the preparation will be in the form of syrup, emulsion, soft gelatin capsule, sterile injectable solution or suspension in an ampoule or vial or non-aqueous liquid suspension.

To obtain a stable water-soluble dose form, a pharmaceutically acceptable salt of an inventive agent can be dissolved in an aqueous solution of an organic or inorganic acid. If a soluble salt form is not available, the agent may be dissolved in a suitable cosolvent or combinations of cosolvents.

It will be appreciated that the actual dosages of the agents used in the compositions of this invention will vary according to the particular complex being used, the particular composition formulated, the mode of administration and the particular site, host and disease being treated. Optimal dosages for a given set of conditions can be ascertained by those skilled in the art using conventional dosage determination tests in view of the experimental data for an agent.

The compositions of the invention may be manufactured in manners generally known for preparing pharmaceutical compositions, e.g., using conventional techniques such as mixing, dissolving, granulating, dragee-making, levigating, emulsifying, encapsulating, entrapping or lyophilizing. Pharmaceutical compositions may be formulated in a conventional manner using one or more physiologically acceptable carriers, which may be selected from excipients and auxiliaries that facilitate processing of the active compounds into preparations which can be used pharmaceutically.

For oral administration, the compounds can be formulated readily by combining the compounds with pharmaceutically acceptable carriers known in the art. Such carriers enable the compounds of the invention to be formulated as tablets, pills, dragees, capsules, liquids, gels, syrups, slurries, suspensions and the like, for oral ingestion by a patient to be treated. Pharmaceutical preparations for oral use can be obtained using a solid excipient in admixture with the active ingredient (agent), optionally grinding the resulting mixture, and processing the mixture of granules after adding suitable auxiliaries, if desired, to obtain tablets or dragee cores.

EXAMPLES

Example 1

5-[1-Quinazolin-6-yl-meth-(Z)-ylidene]-2-[(thiophen-2-ylmethyl)-amino]-thiazol-4-one

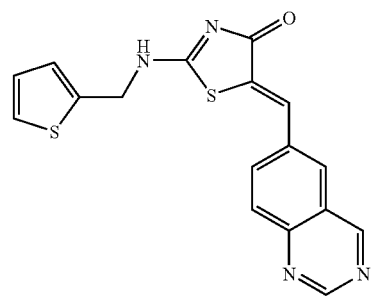

a) Preparation of 6-quinazolinecarboxaldehyde

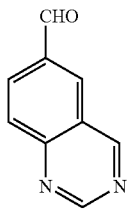

The mixture of 6-methyl-quinazoline (5.0 g, 34.7 mmol) and selenium dioxide (7.7 g, 69.4 mmol) was heated at 160° C. for 12 hours. After cooling to room temperature, methanol was added with stirring. After removal of solid by filtration, the filtrate was concentrated. Flash chromatography (Merck Silica gel 60, 230-400 mesh, 0%-30% ethyl acetate in hexane in 30 min) afforded 6-quinazolinecarboxaldehyde (2.4 g, 43.7%) as a white solid: LC-MS m/e 159 (MH$^+$).

b) Preparation of 5-quinazolin-6-ylmethylene-2-thioxo-thiazolidin-4-one

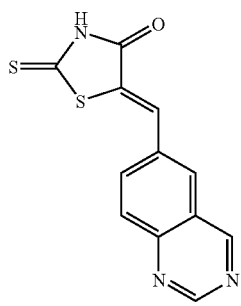

The suspension of 6-quinazolinecarboxaldehyde (example 1a, 1.5 g, 9.5 mmol), rhodanine (1.26 g, 9.5 mmol) and sodium acetate (3.11 g, 38 mmol) in acetic acid (10 mL) was stirred at 130° C. for 12 h. After cooling to room temperature, water (40 mL) was added. The solid was collected by filtration, washed with water and dried to obtain 5-quinazolin-6-ylmethylene-2-thioxo-thiazolidin-4-one (2.6 g, 100%) as a solid. LC-MS m/e 274 (MH$^+$).

c) Preparation of 2-methylsulfanyl-5-quinazolin-6-ylmethylene-thiazol-4-one

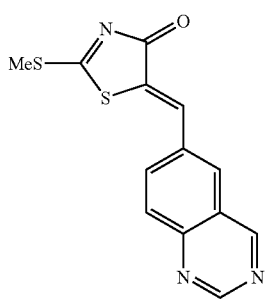

The suspension of 5-quinazolin-6-ylmethylene-2-thioxo-thiazolidin-4-one (example 1b, 2.6 g, 9.52 mmol), iodomethane (1.2 mL, 19.0 mmol) and diisopropylethylamine (DIEA) (2.4 mL, 14.3 mmol) in anhydrous ethanol (100 mL) was stirred at room temperature for 12 h. After adding water (200 mL), the solid was collected by filtration, washed with water and dried to obtain 2-methylsulfanyl-5-quinazolin-6-ylmethylene-thiazol-4-one (2.5 g, 92%) as a black solid. LC-MS m/e 288 (MH$^+$).

d) Preparation of 5-[1-quinazolin-6-yl-meth-(Z)-ylidene]-2-[(thiophen-2-ylmethyl)-amino]-thiazol-4-one The suspension of 2-methylsulfanyl-5-quinazolin-6-ylmethylene-thiazol-4-one (example 1c, 58 mg, 0.2 mmol), thiophene methyl amine (45.3 mg, 0.4 mmol) and diisopropylethylamine (DIEA) (70 uL, 0.4 mmol) in acetonitrile (1 mL) was heated to 145° C. by microwave for 20 min. After cooling to room temperature, the solid was collected by filtration, washed with a small amount of acetonitrile and dried. Flash chromatography (Merck Silica gel 60, 230-400 mesh, 0%-5% methanol in methylene chloride in 30 min) afforded 5-[1-quinazolin-6-yl-meth-(Z)-ylidene]-2-[(thiophen-2-ylmethyl)-amino]-thiazol-4-one as a light yellow solid: LC-MS m/e 353 (MH$^+$).

Example 2

5-[1-Quinazolin-6-yl-meth-(Z)-ylidene]-2-(thiazol-2-ylamino)-thiazol-4-one

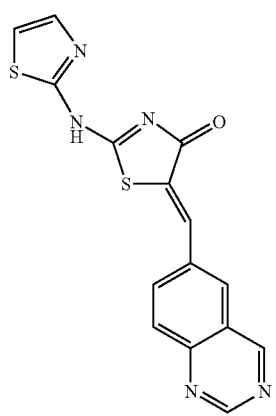

Similar procedure as described in example 1d was used, starting from 2-methylsulfanyl-5-quinazolin-6-ylmethylene-thiazol-4-one, thiazol-2-ylamine and DIEA to give 5-[1-quinazolin-6-yl-meth-(Z)-ylidene]-2-(thiazol-2-ylamino)-thiazol-4-one: LC-MS m/e observed. LC-MS m/e 340 (MH$^+$).

Example 3

2-[2-(3-Fluoro-phenyl)-ethylamino]-5-[1-quinazolin-6-yl-meth-(Z)-ylidene]-thiazol-4-one

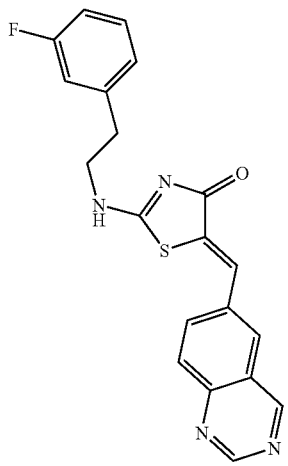

Similar procedure as described in example 1d was used, starting from 2-methylsulfanyl-5-quinazolin-6-ylmethylene-thiazol-4-one, 2-(3-fluoro-phenyl)-ethylamine and DIEA to give 2-[2-(3-fluoro-phenyl)-ethylamino]-5-[1-quinazolin-6-yl-meth-(Z)-ylidene]-thiazol-4-one: LC-MS m/e observed. LC-MS m/e 379 (MH$^+$).

Example 4

2-(2-Ethoxy-phenylamino)-5-[1-quinazolin-6-yl-meth-(Z)-ylidene]-thiazol-4-one

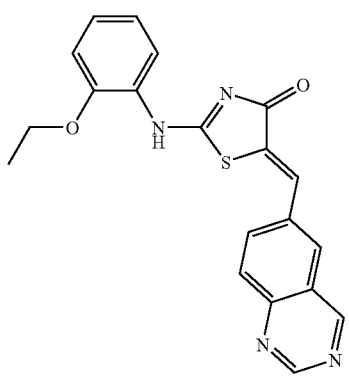

Similar procedure as described in example 1d was used, starting from 2-methylsulfanyl-5-quinazolin-6-ylmethylene-thiazol-4-one, 2-ethoxyaniline and DIEA to give 2-(2-ethoxy-phenylamino)-5-[1-quinazolin-6-yl-meth-(Z)-ylidene]-thiazol-4-one: LC-MS m/e observed. LC-MS m/e 377 (MH$^+$).

Example 5

2-(4-Fluoro-2-methoxy-phenylamino)-5-[1-quinazolin-6-yl-meth-(Z)-ylidene]-thiazol-4-one

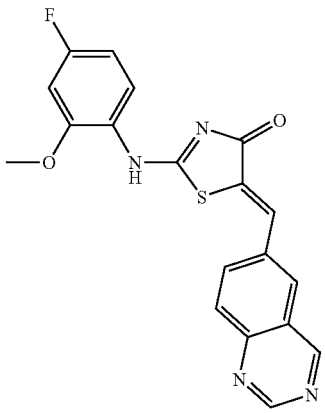

Similar procedure as described in example 1d was used, starting from 2-methylsulfanyl-5-quinazolin-6-ylmethylene-thiazol-4-one, 4-fluoro-2-methoxy-aniline and DIEA to give 2-(4-fluoro-2-methoxy-phenylamino)-5-[1-quinazolin-6-yl-meth-(Z)-ylidene]-thiazol-4-one: LC-MS m/e observed. LC-MS m/e 381 (MH$^+$).

Example 6

2-(3-Fluoro-phenylamino)-5-[1-quinazolin-6-yl-meth-(Z)-ylidene]-thiazol-4-one

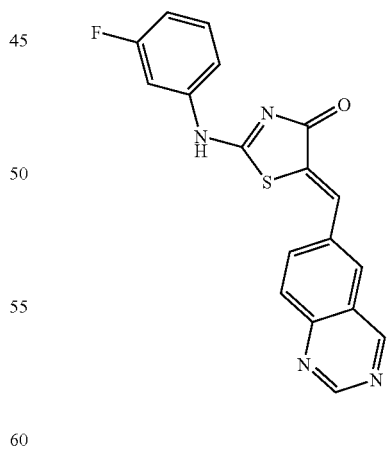

Similar procedure as described in example 1d was used, starting from 2-methylsulfanyl-5-quinazolin-6-ylmethylene-thiazol-4-one, 3-fluoroaniline and DIEA to give 2-(3-fluoro-phenylamino)-5-[1-quinazolin-6-yl-meth-(Z)-ylidene]-thiazol-4-one: LC-MS m/e observed. LC-MS m/e 351 (MH$^+$).

Example 7

2-((R)-1-Hydroxymethyl-2-phenyl-ethylamino)-5-[1-quinazolin-6-yl-meth-(Z)-ylidene]-thiazol-4-one

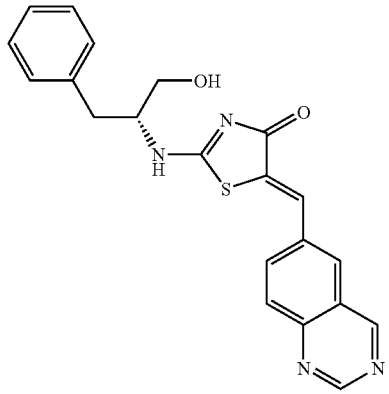

Similar procedure as described in example 1d was used, starting from 2-methylsulfanyl-5-quinazolin-6-ylmethylene-thiazol-4-one, 2-((R)-1-hydroxymethyl-2-phenyl-ethylamine and DIEA to give 2-((R)-1-hydroxymethyl-2-phenyl-ethylamino)-5-[1-quinazolin-6-yl-meth-(Z)-ylidene]-thiazol-4-one: LC-MS m/e observed. LC-MS m/e 391 (MH$^+$).

Example 8

2-(3-Fluoro-benzylamino)-5-[1-quinazolin-6-yl-meth-(Z)-ylidene]-thiazol-4-one

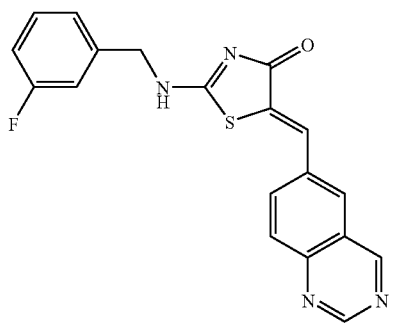

Similar procedure as described in example 1d was used, starting from 2-methylsulfanyl-5-quinazolin-6-ylmethylene-thiazol-4-one, 3-fluoro-benzylamine and DIEA to give 2-(3-fluoro-benzylamino)-5-[1-quinazolin-6-yl-meth-(Z)-ylidene]-thiazol-4-one: LC-MS m/e observed. LC-MS m/e 379 (MH$^+$).

Example 9

2-(2,4-Dimethoxy-phenylamino)-5-[1-quinazolin-6-yl-meth-(Z)-ylidene]-thiazol-4-one

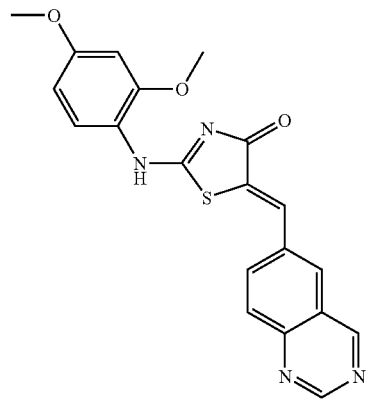

Similar procedure as described in example 1d was used, starting from 2-methylsulfanyl-5-quinazolin-6-ylmethylene-thiazol-4-one, 2,4-dimethoxy-phenylamine and DIEA to give 2-(2,4-dimethoxy-phenylamino)-5-[1-quinazolin-6-yl-meth-(Z)-ylidene]-thiazol-4-one: LC-MS m/e observed. LC-MS m/e 393 (MH$^+$).

Example 10

5-[1-(4-Ethoxy-quinazolin-6-yl)-meth-(Z)-ylidene]-2-[2-(3-fluoro-phenyl)-ethylamino]-thiazol-4-one

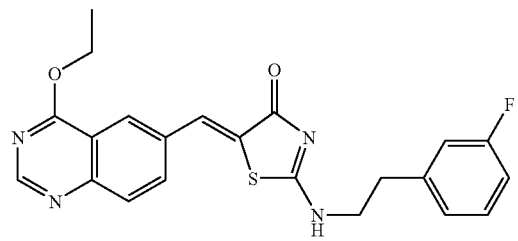

a) Preparation of 6-bromo-4-ethoxy-quinazoline

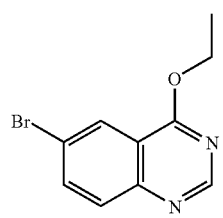

The suspension of 6-bromo-4-chloro-quinazoline (4.87 g, 20 mmol), sodium ethoxide (95%, 14.32 g, 200 mmol) in anhydrous ethyl alcohol (150 ml) was stirred at room temperature for 4 hr. After the reaction, solvent was evaporated. Then, ice water was added, followed by addition of 3 N HCL aq to adjust the pH to 9, and precipitate formed. The solid was collected and washed with H$_2$O three times, then dried. Flash chromatography (Merck silica gel 60, 230-400 mesh, 10%-50% ethyl acetate in hexane for 30 min) afforded 6-Bromo-4-ethoxy-quinazoline (2.13 g, 55%) as a light yellow solid. LC-MS m/e 254 (MH+).

b) Preparation of 4-ethoxy-quinazoline-6-carbaldehyde

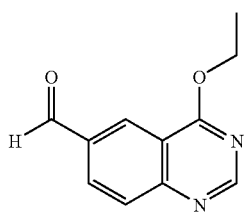

The mixture of 6-bromo-4-ethoxy-quinazoline (example 10a, 506 mg, 2 mmol,), diphenylpropyl phosphine (45.6 mg, 0.2 mmol), palladium acetate (44.8 mg, 0.2 mmol) and triethyl amine (505 mg, 5 mmol) in anhydrous N,N-dimethylformamide (DMF) (25 ml) was charged with carbon monoxide at 75 psi. After the above reaction mixture was stirred at room temperature for 15 min, the carbon monoxide was released, and trihexylsilane (1140 mg, 4 mmol) was added. The resulted reaction mixture was charged with carbon monoxide at 75 psi, and heated at 80° C. for 18 hr. After cooling the reaction to room temperature, dichlormethane was added. The resulted solution was extracted with water for 3 times. Organic layer was collected and concentrated to give a yellow solid. Flash chromatography (Merck silica gel 60, 230-400 mesh, 10%-40% ethyl acetate in hexane for 40 min) gave 4-ethoxy-quinazoline-6-carbaldehyde (256 mg, 66%) as a light yellow solid. LC-MS m/e 203 (MH+).

c) Preparation of 2-[(3-fluorophenyl)-ethylamino]-thiazol-4-one

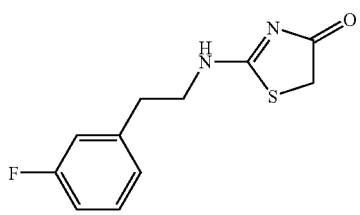

To a solution of (3-fluorophenyl)-ethylamine (3.06 g, 22 mmol) and rhodanine (2.66 g, 20 mmol) in acetonitrile (70 mL) was added DIEA (7.66 mL, 44 mmol) at room temperature. Then, this solution was cooled to 0° C. and mercuric chloride (5.97 g, 22 mmol) was added in two portions. After addition, the suspension was allowed to warm to room temperature and stirred for 3 days. The resulting black solids were filtered through a plug of celite and washed with dichloromethane (500 mL) and methanol (250 mL). The combined solvents were removed under the vacuum and the crude residue was dissolved in ethyl acetate (25 mL) at hot condition and stored in the refrigerator overnight. Then, the solids were collected by filtration and washed with ethyl acetate. After drying in air, 3.65 g (76.6% yield) of 2-[(3-fluorophenyl)-ethylamino]-thiazol-4-one was isolated as a white amorphous solid: HRES(+) m/e calcd for $C_{11}H_{11}FN_2OS$ (M+H)+ 239.0649, found 239.0647.

d) Preparation of 5-[1-(4-ethoxy-quinazolin-6-yl)-meth-(Z)-ylidene]-2-[2-(3-fluoro-phenyl)-ethylamino]-thiazol-4-one

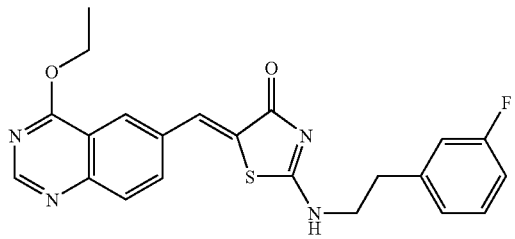

The mixture of 4-ethoxy-quinazoline-6-carbaldehyde (example 10b, 20 mg, 0.1 mmol,), 2-[2-(3-Fluoro-phenyl)-ethylamino]-thiazol-4-one (example 10c, 24 mg, 0.1 mmol) and piperidine (10 ul, 0.1 mmol) in anhydrous ethyl alcohol (1 ml) was microwaved at 160° C. for 25 min. After cooling the reaction to room temperature, the solid was collected by filtration, then washed with MeOH and dried to afford 5-[1-(4-ethoxy-quinazolin-6-yl)-meth-(Z)-ylidene]-2-[2-(3-fluoro-phenyl)-ethylamino]-thiazol-4-one (12 mg, 30%) as light yellow solid. LC-MS m/e 423 (MH+).

Example 11

2-Amino-5-[1-(4-ethoxy-quinazolin-6-yl)-meth-(Z)-ylidene]-thiazol-4-one

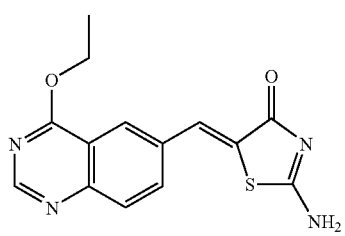

The suspension of 4-ethoxy-quinazoline-6-carbaldehyde (example 10b) (1 equiv.), pseudothiohydantoin (1 equiv.), and sodium acetate (4 equiv.) in acetic acid was stirred under reflux for 12 h. After cooling to room temperature, water was added. The solid was collected by filtration, washed with water and dried to 2-amino-5-[1-(4-ethoxy-quinazolin-6-yl)-meth-(Z)-ylidene]-thiazol-4-one. LC-MS m/e 301 (MH+) as a slight yellow solid. LC-MS m/e 256 (MH+).

Example 12

5-[1-(4-Ethoxy-2-methylamino-quinazolin-6-yl)-meth-(Z)-ylidene]-2-((1R,2S)-2-phenyl-cyclopropylamino)-thiazol-4-one

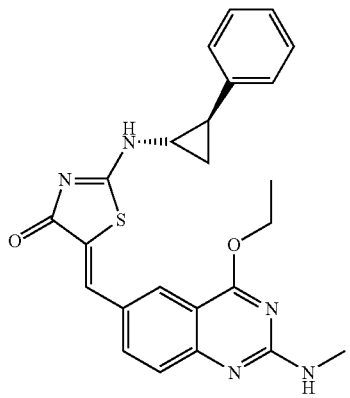

a) Preparation of 2-((1R,2S)-2-phenyl-cyclopropylamino)-thiazol-4-one

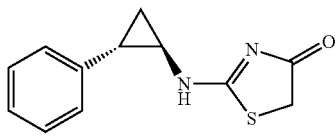

Similar procedure as described in example 10c was used, starting with (1R,2S)-2-phenyl-cyclopropylamine, rhodanine, mercuric chloride and DIEA to give 2-((1R,2S)-2-phenyl-cyclopropylamino)-thiazol-4-one. LC-MS m/e 232 (MH$^+$).

b) Preparation of 6-bromo-1H-benzo[d][1,3]oxazine-2,4-dione

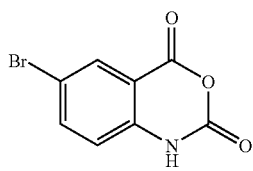

To a suspension of 2-amino-5-bromo-benzoic acid (270 g, 1.25 mol) in acetonitrile (1250 mL) was added a solution of triphosgene (123.8 g, 416.7 mmol) in dichloromethane (DCM) (500 mL) and pyridine (197.5 g, 2.5 mol) simultaneously at 55° C. The resultant mixture was stirred for another 3 hours then cooled to room temperature. The precipitate was collected by filtration, washed with acetonitrile and dried to afford 6-bromo-1H-benzo[d][1,3]oxazine-2,4-dione as a pale powder (280 g, 93%). $^1$H NMR (DMSO-d$_6$): δ 11.83 (s, 1H), 7.98 (s, 1H), 7.89-7.87 (d, 1H,), 7.09-7.07 (d, 1H).

c) Preparation of 6-bromo-2-methylamino-1H-quinazolin-4-one

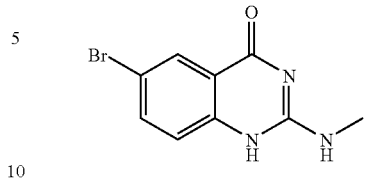

To a combined solution of acetonitrile (360 mL) and water (90 mL) was added 6-bromo-1H-benzo[d][1,3]oxazine-2,4-dione (24.2 g, 0.1 mol), 1,2-dimethyl-isothiourea hydriodic (23.2 g, 0.1 mol) followed by anhydrous sodium carbonate (11.7 g, 0.11 mol) and the mixture was heated to reflux for 3 hours. After cooling down, the precipitate was collected by filtration, washed with water to afford 6-bromo-2-methylamino-1H-quinazolin-4-one (16.5 g, 65 mmol, 65%) as a light yellow powder. $^1$H NMR (DMSO-d$_6$): δ 11.20 (b, 1H), 7.91-7.90 (d, 1H), 7.64-7.63 (d, 1H), 7.20-7.18 (d, 1H), 6.30 (b, 1H), 2.82-2.81 (d, 3H).

d) Preparation of (6-bromo-4-chloro-quinazolin-2-yl)-methyl-amine

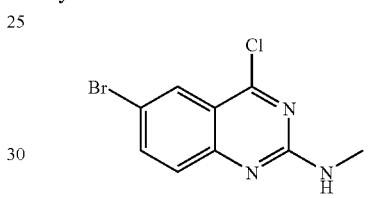

To a solution of phosphorus oxychloride (50 mL) was added powdered 6-bromo-2-methylamino-1H-quinazolin-4-one (10.0 g, 39.4 mmol) followed by dimethyl-phenyl-amine (8 mL) and the mixture was heated to reflux under N$_2$ atmosphere for half an hour. After cooling down, the mixture was poured onto ice and basified with aqueous NaOH solution (2 M). The precipitate was collected by filtration and purified by column to afford (6-bromo-4-chloro-quinazolin-2-yl)-methyl-amine (5 g, 18.3 mmol, 46.6%) as a yellow solid. $^1$H NMR (DMSO-d$_6$): δ 8.03 (s, 1H), 7.86-7.84 (m, 2H), 7.47-7.45 (d, 1H), 2.86-2.84 (d, 3H).

e) Preparation of (6-bromo-4-ethoxy-quinazolin-2-yl)-methyl-amine

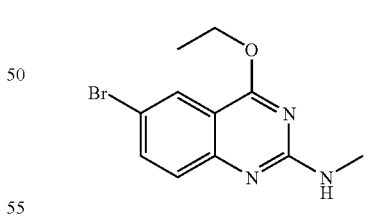

To a solution of sodium ethoxide (8.11 g, 119.3 mmol) in absolute alcohol (150 mL) was added powder (6-bromo-4-chloro-quinazolin-2-yl)-methyl-amine (13 g, 47.7 mmol) in one portion and the mixture was stirred for 3 hours at room temperature under N$_2$ atmosphere. The excess of alcohol was removed in vacuo and the residue was purified by column to afford (6-bromo-4-ethoxy-quinazolin-2-yl)-methyl-amine (4 g, 14.2 mmol, 29.8%) as a light yellow solid. $^1$H NMR (DMSO-d$_6$): δ 7.90-7.89 (d, 1H), 7.70-7.67 (dd, 1H), 7.33-7.31 (m, 1H), 7.21-7.20 (dd, 1H), 4.45-4.44 (q, 2H), 2.83-2.82 (d, 3H), 1.40-1.37 (t, 3H).

f) Preparation of 4-ethoxy-2-methylamino-quinazoline-6-carbaldehyde

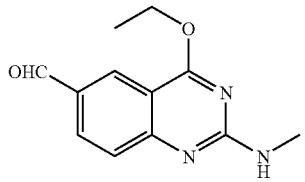

To a combined solution of acetonitrile (40 mL) and DMSO (40 mL) was added tetrakis(triphenylphosphine)palladium (0) (1.65 g, 1.43 mmol), anhydrous sodium formate (5.82 g, 85.6 mmol) followed by powder (6-bromo-4-ethoxy-quinazolin-2-yl)-methyl-amine (4 g, 14.3 mmol) and the resultant mixture was heated to 85° C., 50 psi under CO atmosphere. After being stirred for 48 hours, the cooled mixture was poured to water and extracted with DCM (3×200 mL). The combined organic phase was washed with brine, dried over Na$_2$SO$_4$, evaporated to give a brown solid which was purified by column to afford 4-ethoxy-2-methylamino-quinazoline-6-carbaldehyde (1 g, 4.3 mmol, 30%) as a pale solid. $^1$H NMR (DMSO-d$_6$): δ 9.95 (s, 1H), 8.38 (s, 1H), 8.00-7.97 (d, 1H), 7.59-7.56 (m, 1H), 7.46-7.44 (d, 1H), 4.53-4.48 (q, 2H), 2.89-2.87 (d, 3H), 1.44-1.40 (t, 3H).

g) Preparation of 5-[1-(4-ethoxy-2-methylamino-quinazolin-6-yl)-meth-(Z)-ylidene]-2-((1R,2S)-2-phenyl-cyclopropylamino)-thiazol-4-one To a suspension of 2-(trans)-phenylcyclopylamino-thiazol-4-one (example 12a, 38.0 mg, 0.16 mmole), and 4-ethoxy-2-methylamino-quinazoline-6-carbaldehyde (example 12f, 45.5 mg, 0.20 mmole) in 2 mL of toluene in a microwave tube were added benzoic acid (2.0 mg, 0.016 mmole) and piperidine (1.5 mg, 0.02 mmole). The reaction mixture was heated to 150° C. with microwave for 1 h. The reaction mixture was then cooled to r.t. and diluted with toluene. The solid was collected by filtration and the solid was washed with toluene, CH$_2$Cl$_2$ and ether to give 5-[1-(4-ethoxy-2-methylamino-quinazolin-6-yl)-meth-(Z)-ylidene]-2-((1R,2S)-2-phenyl-cyclopropylamino)-thiazol-4-one as a brown solid: 52 mg (72.9%), MS: m/e 446 (MH$^+$).

Example 13

2-(2-Chloro-benzylamino)-5-(4-ethoxy-2-methylamino-quinazolin-6-ylmethylene)-thiazol-4-one

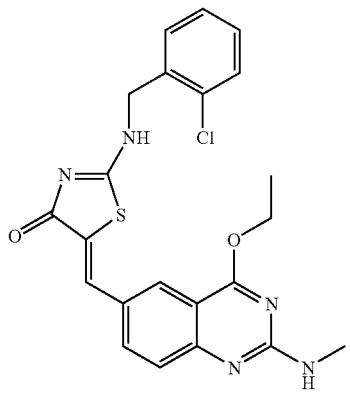

a) Preparation of 2-(2-chloro-benzylamino)-thiazol-4-one

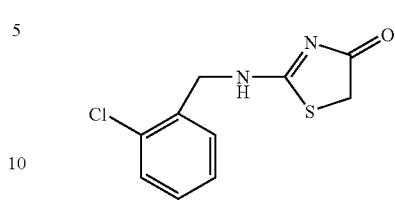

Similar procedure as described in example 10c was used, starting with 2-chloro-benzylamine, rhodanine, mercuric chloride and DIEA to give 2-(2-chloro-benzylamino)-thiazol-4-one. LC-MS m/e 241 (MH$^+$).

b) Preparation of 2-(2-chloro-benzylamino)-5-(4-ethoxy-2-methylamino-quinazolin-6-ylmethylene)-thiazol-4-one To a suspension of 2-(2-chloro-benzylamino)-thiazol-4-one (example 13a, 38.5. mg, 0.16 mmole), and 4-ethoxy-2-methylamino-quinazoline-6-carbaldehyde (example 12f, 45.5 mg, 0.20 mmole) in 2 mL of toluene in a microwave tube were added benzoic acid (2.0 mg, 0.016 mmole) and piperidine (1.5 mg, 0.02 mmole). The reaction mixture was heated to 150° C. with microwave for 45 min. The reaction mixture was then cooled to r.t. and the solid was filtered off, washed with toluene, MeOH and ether to give 2-(2-chloro-benzylamino)-5-(4-ethoxy-2-methylamino-quinazolin-6-ylmethylene)-thiazol-4-one as a brown solid: 43.2 mg (59.5%), MS: m/e 454 (MH$^+$).

Example 14

2-Amino-5-(4-ethoxy-2-methylamino-quinazolin-6-ylmethylene)-thiazol-4-one

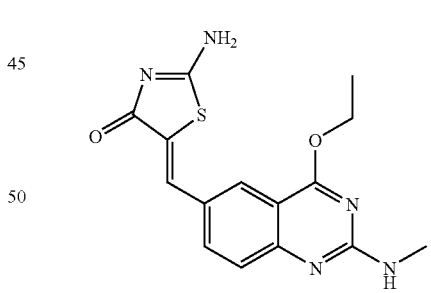

To a suspension of pseudothiohydontoin (40.6 mg, 0.35 mmole), 4-ethoxy-2-methylamino-quinazoline-6-carbaldehyde (example 12f, 81.0 mg, 0.35 mmole) and NaOAc (82.0 mg, 1.0 mmole) in 2.5 mL of xylene was added acetic acid (78.6 mg, 1.3 mmole). The reaction mixture was heated under refluxing overnight. The reaction mixture was then cooled to r.t. and the solid was filtered off, washed with MeCN to give the crude product which was triturated with 2-amino-5-(4-ethoxy-2-methylamino-quinazolin-6-ylmethylene)-thiazol-4-one as a brown solid: 4.5 mg (3.9%), MS: m/e 330 (MH$^+$).

Example 15

5-(4-Ethoxy-2-methylamino-quinazolin-6-ylmethylene)-2-[(3-methyl-thiophen-2-ylmethyl)-amino]-thiazol-4-one

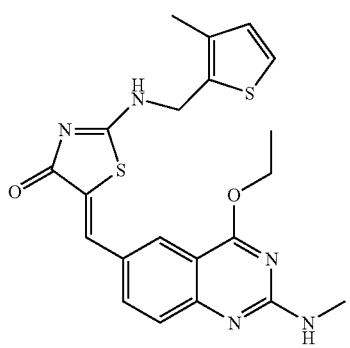

a) Preparation of 2-[(3-methyl-thiophen-2-ylmethyl)-amino]-thiazol-4-one

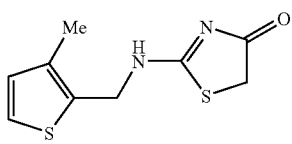

To a solution of 3-methyl-thiophen-2-ylmethylamine (700 mg, 5.5 mmol) and rhodanine (732 mg, 5.5 mmol) in acetonitrile (30 mL) was added diisopropylethylamine (DIEA) (1.91 mL, 11 mmol) at room temperature. Then, this solution was cooled to 0° C. and mercuric chloride (1.52 g, 5.6 mmol) was added in one portion. After addition, the suspension was allowed to warm to room temperature and stirred for 3 days. The resulting black solids were filtered through a plug of celite and washed with acetonitrile (200 mL) and ethyl acetate (250 mL). The filtrates were removed under the vacuum and the crude residue was dissolved in dichloromethane (150 mL) and washed with water and brine solution. After drying over magnesium sulfate, the filtrate was removed under the vacuum and the residue was dissolved in dichloromethane (10 mL) and diluted with hexanes (10 mL). After overnight storage in the refrigerator, the solids were collected by filtration and washed with dichloromethane. After drying in air, 390 mg (31.5% yield) of 2-[(3-methyl-thiophen-2-ylmethyl)-amino]-thiazol-4-one was isolated as a light yellow amorphous solid: EI-HRMS m/e calcd for $C_9H_{10}N_2OS_2$ ($M^+$) 226.0235, found 226.0232.

b) Preparation of 5-(4-ethoxy-2-methylamino-quinazolin-6-ylmethylene)-2-[(3-methyl-thiophen-2-ylmethyl)-amino]-thiazol-4-one To a suspension of 2-[(3-methyl-thiophen-2-ylmethyl)-amino]-thiazol-4-one (36.2. mg, 0.16 mmole), and 4-ethoxy-2-methylamino-quinazoline-6-carbaldehyde (example 12f, 45.5 mg, 0.20 mmole) in 2 mL of toluene in a microwave tube were added benzoic acid (2.0 mg, 0.016 mmole) and piperidine (1.5 mg, 0.02 mmole). The reaction mixture was heated to 150° C. with microwave for 45 min. The reaction mixture was then cooled to r.t. and the solid was filtered off, washed with toluene, MeOH and ether to give 5-(4-ethoxy-2-methylamino-quinazolin-6-ylmethylene)-2-[(3-methyl-thiophen-2-ylmethyl)-amino]-thiazol-4-one as a brown solid: 56.5 mg (80.4%), MS: m/e 440 ($MH^+$).

Example 16

2-(3-Chloro-4-fluoro-benzylamino)-5-(4-ethoxy-2-methylamino-quinazolin-6-ylmethylene)-thiazol-4-one

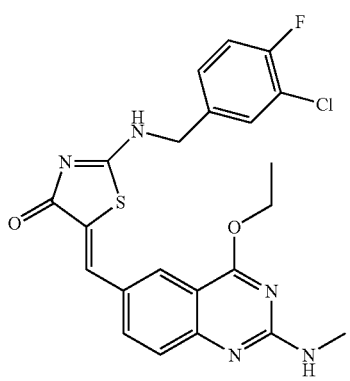

a) Preparation of 2-(3-chloro-4-fluoro-benzylamino)-thiazol-4-one

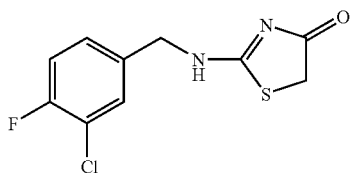

Similar procedure as described in example 15a was used, starting with 3-chloro-4-fluoro-benzylamine, rhodanine, mercuric chloride and DIEA to give 2-(3-chloro-4-fluoro-benzylamino)-thiazol-4-one. LC-MS m/e 259 ($MH^+$).

b) Preparation of 2-(3-chloro-4-fluoro-benzylamino)-5-(4-ethoxy-2-methylamino-quinazolin-6-ylmethylene)-thiazol-4-one To a suspension of 2-(3-chloro-4-fluoro-benzylamino-thiazol-4-one (example 16a, 41.4 mg, 0.16 mmole), and 4-ethoxy-2-methylamino-quinazoline-6-carbaldehyde (example 12f, 45.5 mg, 0.20 mmole) in 2 mL of toluene in a microwave tube were added benzoic acid (2.0 mg, 0.016 mmole) and piperidine (1.5 mg, 0.02 mmole). The reaction mixture was heated to 150° C. with microwave for 30 min. The reaction mixture was then cooled to r.t. and the solid was filtered off, washed with toluene to give the crude product 58.8 mg (77.9%) which was re-dissolved in 0.5 mL hot DMF and diluted with water at r.t. The precipitates were collected and washed with water, acetone and ether, dried over $NaSO_4$ and concentrated to give 2-(3-chloro-4-fluoro-benzylamino)-5-(4-ethoxy-2-methylamino-quinazolin-6-ylmethylene)-thiazol-4-one as a light yellow solid: 43.6 mg (57.7%), MS: m/e 472 ($MH^+$).

Example 17

2-(2-Chloro-4-fluoro-benzylamino)-5-(4-ethoxy-2-methylamino-quinazolin-6-ylmethylene)-thiazol-4-one

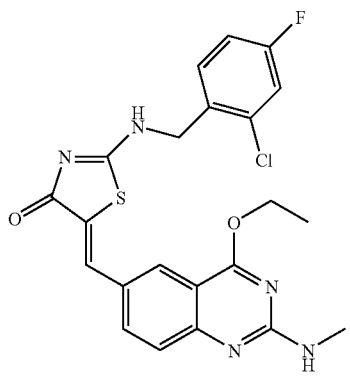

a) Preparation of 2-(2-chloro-4-fluoro-benzylamino)-thiazol-4-one

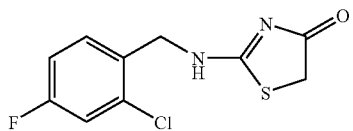

Similar procedure as described in example 15a was used, starting with 2-chloro-4-fluoro-benzylamine, rhodanine, mercuric chloride and DIEA to give 2-(2-chloro-4-fluoro-benzylamino)-thiazol-4-one. LC-MS m/e 259 (MH$^+$).

b) Preparation of 2-(2-chloro-4-fluoro-benzylamino)-5-(4-ethoxy-2-methylamino-quinazolin-6-ylmethylene)-thiazol-4-one To a suspension of 2-(2-chloro-4-fluoro-benzylamino)-thiazol-4-one (example 17a, 41.4 mg, 0.16 mmole), and 4-ethoxy-2-methylamino-quinazoline-6-carbaldehyde (example 12f, 45.5 mg, 0.20 mmole) in 2 mL of toluene in a microwave tube were added benzoic acid (2.0 mg, 0.016 mmole) and piperidine (1.5 mg, 0.02 mmole). The reaction mixture was heated to 150° C. with microwave for 30 min. The reaction mixture was then cooled to r.t. and the solid was filtered off, washed with toluene, MeOH and ether to give 2-(2-chloro-4-fluoro-benzylamino)-5-(4-ethoxy-2-methylamino-quinazolin-6-ylmethylene)-thiazol-4-one as a light brown solid: 46.6 mg (61.7%), MS: m/e 472 (MH$^+$).

Example 18

2-(2-Chloro-6-methyl-benzylamino)-5-(4-ethoxy-2-methylamino-quinazolin-6-ylmethylene)-thiazol-4-one

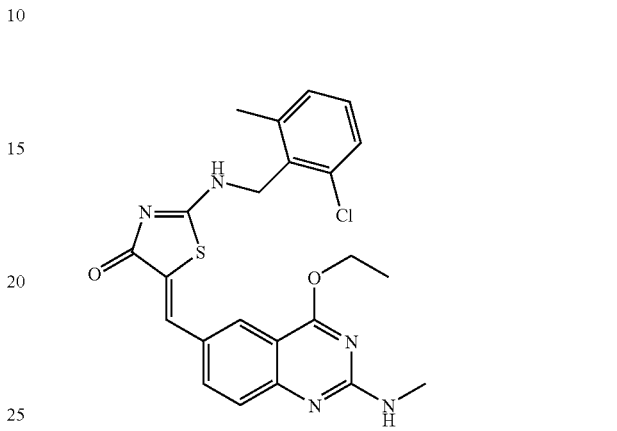

a) Preparation of 2-(2-chloro-6-methyl-benzylamino)-thiazol-4-one

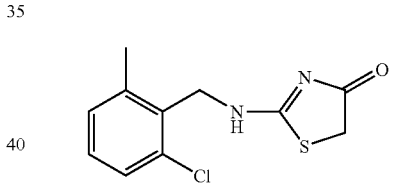

Similar procedure as described in example 15a was used, starting with 2-chloro-6-methyl-benzylamine, rhodanine, mercuric chloride and DIEA to give 2-(2-chloro-6-methyl-benzylamino)-thiazol-4-one. LC-MS m/e 259 (MH$^+$).

b) Preparation of 2-(2-chloro-6-methyl-benzylamino)-5-(4-ethoxy-2-methylamino-quinazolin-6-ylmethylene)-thiazol-4-one To a suspension of 2-(2-chloro-6-methyl-benzylamino)-thiazol-4-one (example 18a, 40.8 mg, 0.16 mmole), and 4-ethoxy-2-methylamino-quinazoline-6-carbaldehyde (example 12f, 45.5 mg, 0.20 mmole) in 2 mL of toluene in a microwave tube were added benzoic acid (2.0 mg, 0.016 mmole) and piperidine (1.5 mg, 0.02 mmole). The reaction mixture was heated to 150° C. with microwave for 30 min. The reaction mixture was then cooled to r.t. and the solid was filtered off, washed with toluene, MeOH and ether to give 2-(2-chloro-6-methyl-benzylamino)-5-(4-ethoxy-2-methylamino-quinazolin-6-ylmethylene)-thiazol-4-one as a light brown solid: 45.9 mg (61.3%), MS: m/e 468 (MH$^+$).

Example 19

5-(4-Ethoxy-2-methylamino-quinazolin-6-ylmethylene)-2-[(thiophen-2-ylmethyl)-amino]-thiazol-4-one

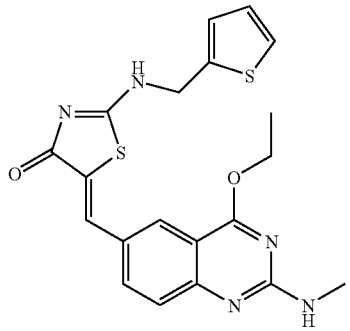

a) Preparation of 2-(thiophen-2-ylmethyl)-amino)-thiazol-4-one

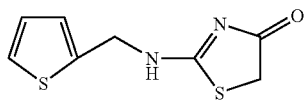

Similar procedure as described in example 15a was used, starting with thiophen-2-ylmethyl-amine, rhodanine, mercuric chloride and DIEA to give 2-(thiophen-2-ylmethyl-amino)-thiazol-4-one. LC-MS m/e 259 (MH$^+$).

b) Preparation of 5-(4-ethoxy-2-methylamino-quinazolin-6-ylmethylene)-2-[(thiophen-2-ylmethyl)-amino]-thiazol-4-one To a suspension of 2-[(thiophen-2-ylmethyl)-amino]-thiazol-4-one (34.0 mg, 0.16 mmole), and 4-ethoxy-2-methylamino-quinazoline-6-carbaldehyde (example 12f, 45.5 mg, 0.20 mmole) in 2 mL of toluene in a microwave tube were added benzoic acid (2.0 mg, 0.016 mmole) and piperidine (1.5 mg, 0.02 mmole). The reaction mixture was heated to 150° C. with microwave for 30 min. The reaction mixture was then cooled to r.t. and the solid was filtered off, washed with toluene, MeOH and ether to give 5-(4-ethoxy-2-methylamino-quinazolin-6-ylmethylene)-2-[(thiophen-2-ylmethyl)-amino]-thiazol-4-one as a brown solid: 48.6 mg (69.1%), MS: m/e 426 (MH$^+$).

Example 20

5-(4-Ethoxy-2-methylamino-quinazolin-6-ylmethylene)-2-[2-(3-fluoro-phenyl)-ethylamino]-thiazol-4-one

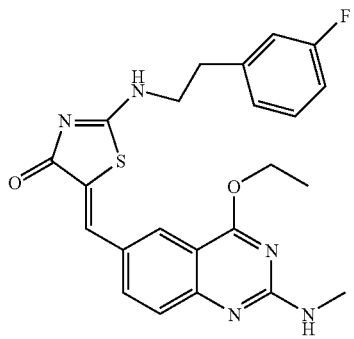

To a suspension of 2-[2-(3-fluoro-phenyl)-ethylamino]-thiazol-4-one (example 10c, 38.1 mg, 0.16 mmole), and 4-ethoxy-2-methylamino-quinazoline-6-carbaldehyde (example 12f, 45.5 mg, 0.20 mmole) in 2 mL of toluene in a microwave tube were added benzoic acid (2.0 mg, 0.016 mmole) and piperidine (1.5 mg, 0.02 mmole). The reaction mixture was heated to 150° C. with microwave for 30 min. The reaction mixture was then cooled to r.t. and the solid was filtered off, washed with toluene, MeOH and ether to give 5-(4-ethoxy-2-methylamino-quinazolin-6-ylmethylene)-2-[2-(3-fluoro-phenyl)-ethylamino]-thiazol-4-one as a light brown solid: 52.3 mg (72.4%), MS: m/e 452 (MH$^+$).

Example 21

The pharmacological properties of the compounds of this invention may be confirmed by a number of pharmacological assays. The exemplified pharmacological assays which follow have been carried out with the compounds according to the invention and their salts. The compounds of the invention exhibited CDK1/Cyclin B activity with Ki values of less than 5.0 μM. This demonstrates that all of these compounds were active to inhibit CDK1/Cyclin B.

Kinase Assays

To determine inhibition of CDK1 activity, either FlashPlate™ (NEN™-Life Science Products) assay or HTRF assay was performed. Both types of kinase assays were carried out using recombinant human CDK1/Cyclin B complex. GST-cyclinB (GST-cycB) and CDK1 cDNA clones in baculovirus vectors were provided by Dr. W. Harper at the Baylor College of Medicine, Houston, Tex. Proteins were co-expressed in High Five™ insect cells and the complex was purified on glutathione Sepharose resin (Pharmacia, Piscataway, N.J.) as previously described (Harper, J. W. et al. Cell 1993, 75, 805-816). A 6×-Histidine tagged truncated form of retinoblastoma (Rb) protein (amino acid 386-928) was used as the substrate for the CDK1/Cyclin B assay (the expression plasmid was provided by Dr. Veronica Sullivan, Department of Molecular Virology, Roche Research Centre, Welwyn Garden City, United Kingdom). The Rb protein is a natural substrate for phosphorylation by CDK1 (see Herwig and Strauss Eur. J. Biochem. Vol. 246 (1997) pp. 581-601 and the references cited therein). The expression of the 62Kd protein was under the control of an IPTG inducible promoter in an M15 *E. coli* strain. Cells were lysed by sonication and purification was carried out by binding lysates at pH 8.0 to a Ni-chelated agarose column pretreated with 1 mM imidazole. The resin was then washed several times with incrementally decreasing pH buffers to pH 6.0, and eluted with 500 mM imidazole. Eluted protein was dialyzed against 20 mM HEPES pH 7.5, 30% glycerol, 200 mM NaCl, and 1 mM DTT. Purified Rb fusion protein stocks were quantitated for protein concentration, aliquoted, and stored at −70° C.

For the FlashPlate kinase assay, 96-well FlashPlates were coated with Rb protein at 10 μg/ml, using 100 μl per well. Plates were incubated at 4° C. overnight or at room temperature for 3 hours on a shaker. To control for nonspecific phosphorylation, one row of wells was coated with 100 μl/well coating buffer (20 mM HEPES, 0.2 M NaCl). Plates were then washed twice with wash buffer (0.01% Tween 20 in phosphate-buffered saline). Compounds to be tested ("test compounds") were added to the wells at 5× final concentration. Reactions were initiated by immediate addition of 40 μl reaction mix (25 mM HEPES, 20 mM MgCl$_2$, 0.002% Tween 20, 2 mM DTT, 1 μM ATP, 4 nM 33P-ATP) and a sufficient amount of enzyme to give counts that were at least 10-fold above background. Plates were incubated at room temperature on a shaker for 30 minutes. Plates were washed four times with the wash buffer, sealed, and counted on the TopCount scintillation counter (Packard Instrument Co., Downers Grove, Ill.]. The percent inhibition of Rb phosphorylation, which is a measure of the inhibition of CDK activity, was determined according to the following formula:

$$100 \times \frac{1 - \text{test compound} - \text{nonspecific}}{\text{total} - \text{nonspecific}}$$

where "test compound" refers to the average counts per minute of the test duplicates, "nonspecific" refers to the average counts per minute when no CDK1/Cyclin B, etc., was added, and "total" refers to the average counts per minute when no compound was added. The $IC_{50}$ value is the concentration of test compound that reduces by 50% the protein-kinase induced incorporation of the radiolabel under the test conditions described. The value of the inhibitor constant Ki is calculated by the following: Ki=IC50/(1+[S]/Km), where [S] is the ATP concentration and Km is Michaelis constant.

The Homogeneous Time Resolved Fluorescence (HTRF) kinase assay was carried out in 96-well polypropylene plates (BD Biosciences, Bedford, Mass.). Test compounds were first dissolved in DMSO, and then diluted in kinase assay buffer 1 (25 mM HEPES, pH7.0, 8 mM $MgCl_2$, 1.5 mM DTT, and 162 µM ATP) with DMSO concentration at 15%. The CDK1/Cyclin B enzyme was diluted in kinase assay buffer 2 (25 mM HEPES, pH 7.0, 8 mM $MgCl_2$, 0.003% Tween 20, 0.045% BSA, 1.5 mM DTT, and 0.338 µM Rb protein). To initiate the kinase reaction, 20 µL of compound solution was mixed with 40 µL of CDK1/Cyclin B solution in assay plates with final concentration of CDK1/Cyclin B and Rb at 0.1 µg/mL and 0.113 µM, respectively, and incubated at 37° C. for 30 min. 15 µL of anti-phospho-Rb (Ser 780) antibody (Cell Signaling Technology, Beverly, Mass.,) was added with a 1:7692 dilution of the antibody. Incubation was continued at 37° C. for 25 min, after which LANCE Eu-W1024 labeled anti-rabbit IgG (1 nM, PerkinElmer, Wellesley, Mass.) and anti-His antibody conjugated to SureLight-Allophucocyanin (20 nM, PerkinElmer, Wellesley, Mass.) were added to the wells. Incubation was continued at 37° C. for another 40 min. At the completion of the incubation, 35 µL of reaction mixture was transferred to fresh 384-well black polystyrene plates (Corning Incorporated, Corning, N.Y.) and read on a fluorescent plate reader at excitation wavelength of 340 nm and emission wavelength of 665/615 nm.

Ki values showing CDK1/Cyclin B activity that applied to compounds of the subject of this invention ranges from about 0.001 µM to about 5.000 µM. Specific data for some examples are as follows:

| Example | Ki (µM) |
|---------|---------|
| 1 | 1.224 |
| 3 | 0.881 |
| 5 | 1.838 |
| 7 | 1.110 |

What is claimed is:
1. A compound having the formula:

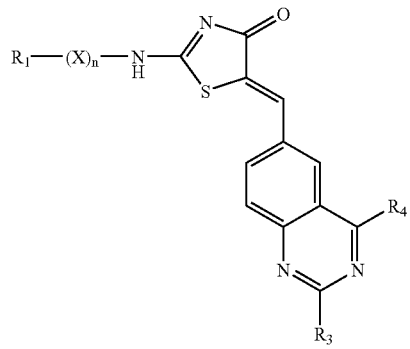

wherein
R₁ is lower alkyl or

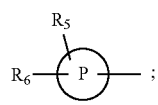

X is selected from lower alkylene, cyclolower alkylene containing from 3 to 6 carbon atoms and hydroxy lower alkylene;

is selected from an aryl ring, cyclolower alkyl ring containing from 3 to 6 carbon atoms, a 4 to 6 membered heterocycloalkyl ring containing from 3 to 5 carbon atoms and from 1 to 2 hetero atoms selected from the group consisting of oxygen, nitrogen and sulfur, and a 5 or 6 membered heteroaromatic ring containing from 1 to 2 hetero atoms selected from the group consisting of oxygen, sulfur and nitrogen;

R₅ and R₆ are independently selected from the group consisting of hydrogen, hydroxy, hydroxy-lower alkyl, lower alkyl, halogen, perfluro-lower alkyl and lower alkoxy;

R₃ is selected from hydrogen, —NHR₇ and

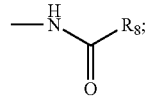

R₄ is selected from hydrogen, lower alkyl and —O(CH₂CH₂O)ᵧ—R₁₀;
R₇ is hydrogen or lower alkyl;
R₈ and R₁₀ are lower alkyl;
n is an integer from 0 to 1; and
y is an integer of from 0 to 3;
with the proviso that when n is 0 and R₁ is lower alkyl then R₃/R₄ cannot both be hydrogen; and N-oxides of compounds where $R_1$ contains a nitrogen in the heteroaromatic ring, sulfones where $R_1$ contains a sulfur in the heterocycloalkyl ring or heteroaromatic ring; and pharmaceutically acceptable salts thereof.

2. The compound of claim 1 wherein said compound has the formula:

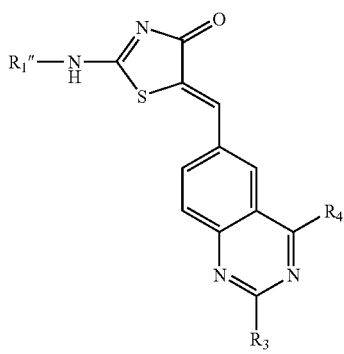

I-B wherein $R_1''$ is 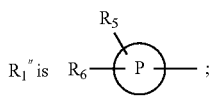 ;

$R_3$, $R_4$, $R_5$, and

are as set forth in claim 1; and

N-oxides of compounds where $R_1''$ contains a nitrogen in the heteroaromatic ring, sulfones where $R_1''$ contains a sulfur in the hetero ring or heteroaromatic ring, and pharmaceutically acceptable salts thereof.

3. The compound of claim 2 wherein $R_1''$ is

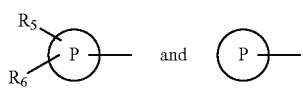

is phenyl.

4. The compound of claim 3 where said compound is selected from the group consisting of 2-(2,4-dimethoxy-phenylamino)-5-[1-quinazolin-6-yl-methylidene]-thiazol-4-one, 2-(2-ethoxy-phenylamino)-5-[1-quinazolin-6-yl-methylidene]-thiazol-4-one, and 2-(4-fluoro-2-methoxy-phenylamino)-5-[1-quinazolin-6-yl -methylidene]-thiazol-4-one.

5. The compound of claim 2 wherein

is a heteroaromatic ring containing from 1 to 2 heteroatoms.

6. The compound of claim 5 wherein ring contains two heteroatoms, one being sulfur and the other being nitrogen.

7. The compound of claim 6 wherein said compound is 5-[1-quinazolin-6-yl-methylidene]-2-(thiazol-2-ylamino)-thiazol-4-one.

8. A compound of claim 1 wherein said compound has the formula:

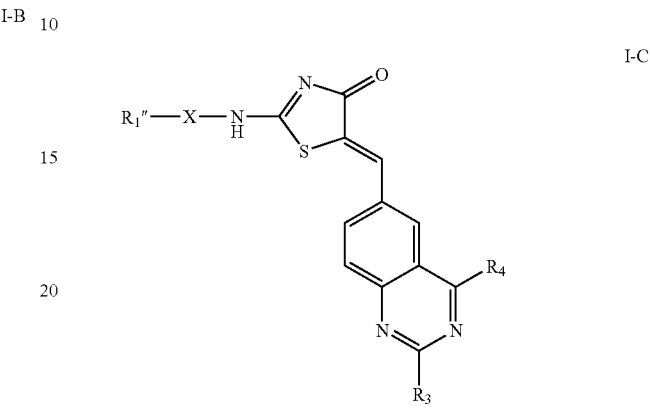

I-C wherein $R_1''$ is $R_1$ $R_1$, X, $R_3$, $R_4$ are as set forth in claim 1, and N-oxides of compounds where $R_1''$ contains a nitrogen in the heteroaromatic ring, sulfones where $R_1''$ contains a sulfur in the hetero ring or heteroaromatic ring; and pharmaceutically acceptable salts thereof.

9. The compound of claim 8 wherein X is lower alkylene.

10. The compound of claim 9 wherein $R_3$ is hydrogen and $R_4$ is hydrogen or $-O(CH_2CH_2O)_y$-$R_{10}$ and y and $R_{10}$ are as above.

11. The compound of claim 10 wherein $R_1''$ is

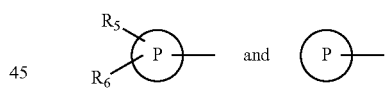

is phenyl.

12. The compound of claim 11 wherein said compound is selected from the group consisting of 2-[2-(3-fluoro-phenyl)-ethylamino]-5-[1-quinazolin-6-yl-methylidene]-thiazol-4-one, 2-(3-fluoro-benzylamino)-5-[1 -quinazolin-6-yl-methylidene]-thiazol-4-one, 5-[1-(4-ethoxy-quinazolin-6-yl)-methylidene]-2-[2-(3-fluoro-phenyl)-ethylamino]-thiazol-4-one, 2-(2-chloro-benzylamino)-5-(4-ethoxy-2-methylamino-quinazolin-6-ylmethylene)-thiazol-4-one, 2-(3-chloro-4-fluoro-benzylamino)-5-(4-ethoxy-2-methylamino-quinazolin-6-ylmethylene)-thiazol-4-one, 2-(2-chloro-4-fluoro-benzylamino)-5-(4-ethoxy-2-methylamino-quinazolin-6-ylmethylene)-thiazol-4-one, 2-(2-chloro-6-methyl-benzylamino)-5-(4-ethoxy-2-methylamino-quinazolin-6-ylmethylene)-thiazol-4-one, and 5-(4-ethoxy-2-methylamino-quinazolin-6-ylmethylene)-2-[2-(3-fluoro-phenyl)-ethylamino]-thiazol-4-one.

13. The compound of claim 9 wherein $R_1''$ is

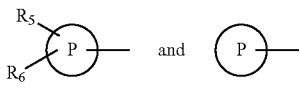

is a heteroaromatic ring containing from 1 to 2 heteroatoms.

14. The compound of claim 13 wherein ring contains two hetero atoms, one being sulfur and the other being nitrogen.

15. The compound of claim 14 wherein said ring is a thiazole ring.

16. The compound of claim 13 wherein ring contains one heteroatom which is a sulfur atom.

17. The compound of claim 16 wherein $R_3$ and $R_4$ are hydrogen.

18. The compound of claim 17 wherein said compound is selected from the group consisting of 5-[1-quinazolin-6-yl-methylidene]-2-[(thiophen-2-ylmethyl)-amino]-thiazol-4-one, 5-(4-ethoxy-2-methylamino-quinazolin-6-ylmethylene)-2-[(3-methyl-thiophen-2-ylmethyl)-amino]-thiazol-4-one, and 5-(4-ethoxy-2-methylamino-quinazolin-6-ylmethylene)-2-[(thiophen-2-ylmethyl)-amino]-thiazol-4-one.

19. The compound of claim 8 wherein X is cyclolower alkylene, $R_1''$ is

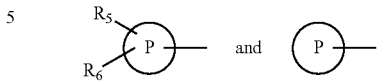

is phenyl.

20. The compound of claim 8 wherein X is hydroxy-loweralkylene.

21. The compound of claim 20 wherein $R_1''$ is

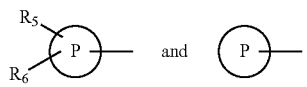

is a phenyl ring.

22. The compound of claim 1 wherein said compound is selected from the group consisting of 2-(1-hydroxymethyl-2-phenyl-ethylamino)-5-[1-quinazolin-6-yl-methylidene]-thiazol-4-one and 5-[1-(4-ethoxy-2-methylamino-quinazolin-6-yl)-meth-(Z)-ylidene]-2-2-phenyl-cyclopropylamino)-thiazol-4-one.

* * * * *

UNITED STATES PATENT AND TRADEMARK OFFICE
CERTIFICATE OF CORRECTION

PATENT NO. : 7,501,428 B2  Page 1 of 1
APPLICATION NO. : 11/244028
DATED : March 10, 2009
INVENTOR(S) : Li Chen, Shaoqing Chen and Jin-Jun Liu It is certified that error appears in the above-identified patent and that said Letters Patent is hereby corrected as shown below:

Column 34, claim 8, line 31, delete "$R_1$"" and insert -- $R_1$ --

Signed and Sealed this

Fourteenth Day of July, 2009

JOHN DOLL
*Acting Director of the United States Patent and Trademark Office*